(12) United States Patent
Abe et al.

(10) Patent No.: US 8,361,058 B2
(45) Date of Patent: Jan. 29, 2013

(54) LASER TREATMENT APPARATUS

(75) Inventors: Hitoshi Abe, Okazaki (JP); Masato Kawai, Okazaki (JP)

(73) Assignee: Nidek Co., Ltd., Gamagori-Shi (JP)

( * ) Notice: Subject to any disclaimer, the term of this patent is extended or adjusted under 35 U.S.C. 154(b) by 546 days.

(21) Appl. No.: 12/382,606

(22) Filed: Mar. 19, 2009

(65) Prior Publication Data

US 2009/0247996 A1    Oct. 1, 2009

(30) Foreign Application Priority Data

Mar. 26, 2008    (JP) .................................. 2008-081694

(51) Int. Cl.
*A61B 18/18*    (2006.01)

(52) U.S. Cl. .................... 606/4; 606/5; 606/10; 606/13; 607/89

(58) Field of Classification Search .................. None
See application file for complete search history.

(56) References Cited

U.S. PATENT DOCUMENTS

| | | | |
|---|---|---|---|
| 5,662,644 A | 9/1997 | Swor | |
| 6,058,130 A | 5/2000 | Shinji et al. | |
| 6,110,165 A | 8/2000 | Ota | |
| 6,636,537 B2 | 10/2003 | Takada | |
| 7,003,001 B2 | 2/2006 | Sharma et al. | |
| 2002/0165525 A1 | 11/2002 | Nakamura | |

FOREIGN PATENT DOCUMENTS

| | | |
|---|---|---|
| GB | 2 369 057 A | 5/2002 |
| JP | A-8-294507 | 11/1996 |
| JP | A-10-209529 | 8/1998 |
| JP | A-2002-151774 | 5/2002 |
| JP | A-2004-321507 | 11/2004 |

*Primary Examiner* — Bill Thomson
*Assistant Examiner* — Lynsey Crandall
(74) *Attorney, Agent, or Firm* — Oliff & Berridge, PLC

(57) ABSTRACT

A laser treatment apparatus for irradiating a laser beam to a patient's eye, comprises: a plurality of laser sources which emit treatment laser beams having different wavelengths, each laser source being held in a main body to be mountable and demountable and connected to a power source through a connector; a light delivery optical system having a mirror for making the laser beams from the laser sources coaxial with each other to deliver each laser beam to the patient's eye; an input unit for inputting mounting information of each laser source; a control unit which checks a predetermined operation of each laser source by a sensor at the time of activation to determine whether an abnormality is present or not in each laser source, and displays an indication that the abnormality is present on a display, wherein the control unit will not perform the operation check whether the abnormality is present or not in the laser source or laser sources unmounted in the main body, based on the mounting information input by the input unit.

10 Claims, 5 Drawing Sheets

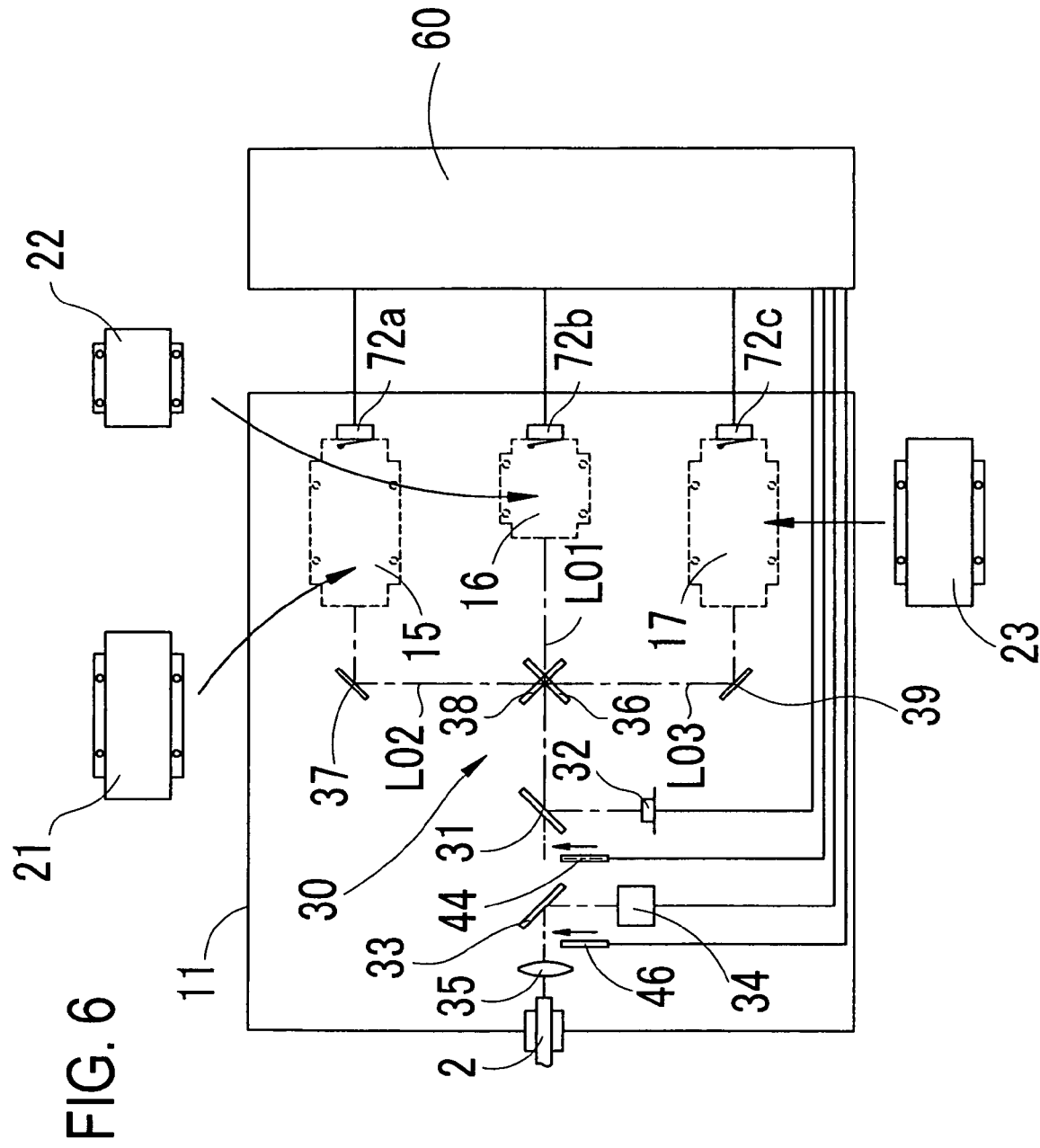

LASER TREATMENT APPARATUS

TECHNICAL FIELD

The present invention relates to a laser treatment apparatus for delivering a laser beam for treatment to a fundus of a patient's eye and others.

BACKGROUND ART

In a laser treatment apparatus for performing coagulation or the like of a fundus of a patient's eye, laser beams having different wavelengths are selectively used according to a disease case and a tissue to be treated. It is therefore convenient to emit laser beams having different wavelengths by a single apparatus. Accordingly, there has been proposed a laser treatment apparatus capable of emitting laser beams having different wavelengths. For example, an apparatus having a single laser source that selectively emits three color laser beams, i.e., green, yellow, and red has been proposed (JP2002-151774A (U.S. Pat. No. 6,636,537)).

Meanwhile, the above apparatus arranged to selectively emit three color laser beams from the single laser source is more complicated in laser source configuration than an apparatus having a laser source that emits a laser beam of a single wavelength and also has a high selling price. Accordingly, in the case where some manufacturers produce an apparatus having a laser source that emits a green beam having a single wavelength and a doctor (a user) mostly conducts treatment on a disease case by using only a green laser beam, the doctor would buy the apparatus having the laser source that emits the green beam having the single wavelength. When the doctor then has to conduct treatment using a yellow laser beam in addition to the green laser beam, the doctor must additionally buy an apparatus having a laser source that emits the yellow laser beam if it is supplied by a manufacturer or an apparatus that emits three color laser beams, green, yellow, and red. If the doctor buys the latter apparatus that emits three color laser beams, this apparatus is expensive because it includes the laser source that emits an unnecessary red laser beam and also the initially bought apparatus having the laser source for the single green wavelength becomes redundant. On the other hand, if the doctor separately buys the laser apparatus for the single green laser beam and the laser apparatus for the single yellow laser beam, a total cost will be higher and an additional footprint is required.

SUMMARY OF INVENTION

Technical Problem

The present invention has been made to solve the above problems and has an object to provide a laser treatment apparatus initially having a laser source that emits a laser beam having a certain wavelength and enabling a doctor or a user to additionally mount another laser source for a different wavelength after purchase of this apparatus, thereby providing economic advantage.

Another object is to provide a laser treatment apparatus that can be used appropriately without causing needless troubles.

Solution to Problem

To achieve the above objects, the present invention provides a laser treatment apparatus for irradiating a laser beam to a patient's eye, comprising: a plurality of laser sources which emit treatment laser beams having different wavelengths, each laser source being held in a main body to be mountable and demountable and connected to a power source through a connector; a light delivery optical system having a mirror for making the laser beams from the laser sources coaxial with each other to deliver each laser beam to the patient's eye; an input unit for inputting mounting information of each laser source; a control unit which checks a predetermined operation of each laser source by a sensor at the time of activation to determine whether an abnormality is present or not in each laser source, and displays an indication that the abnormality is present on a display, wherein the control unit will not perform the operation check whether the abnormality is present or not in the laser source or laser sources unmounted in the main body, based on the mounting information input by the input unit.

BRIEF DESCRIPTION OF DRAWINGS

FIG. 6 is a view to explain a method of recognizing a laser source by use of a sensor for physically detecting presence or absence of each laser source.

DESCRIPTION OF EMBODIMENTS

Figure 1:
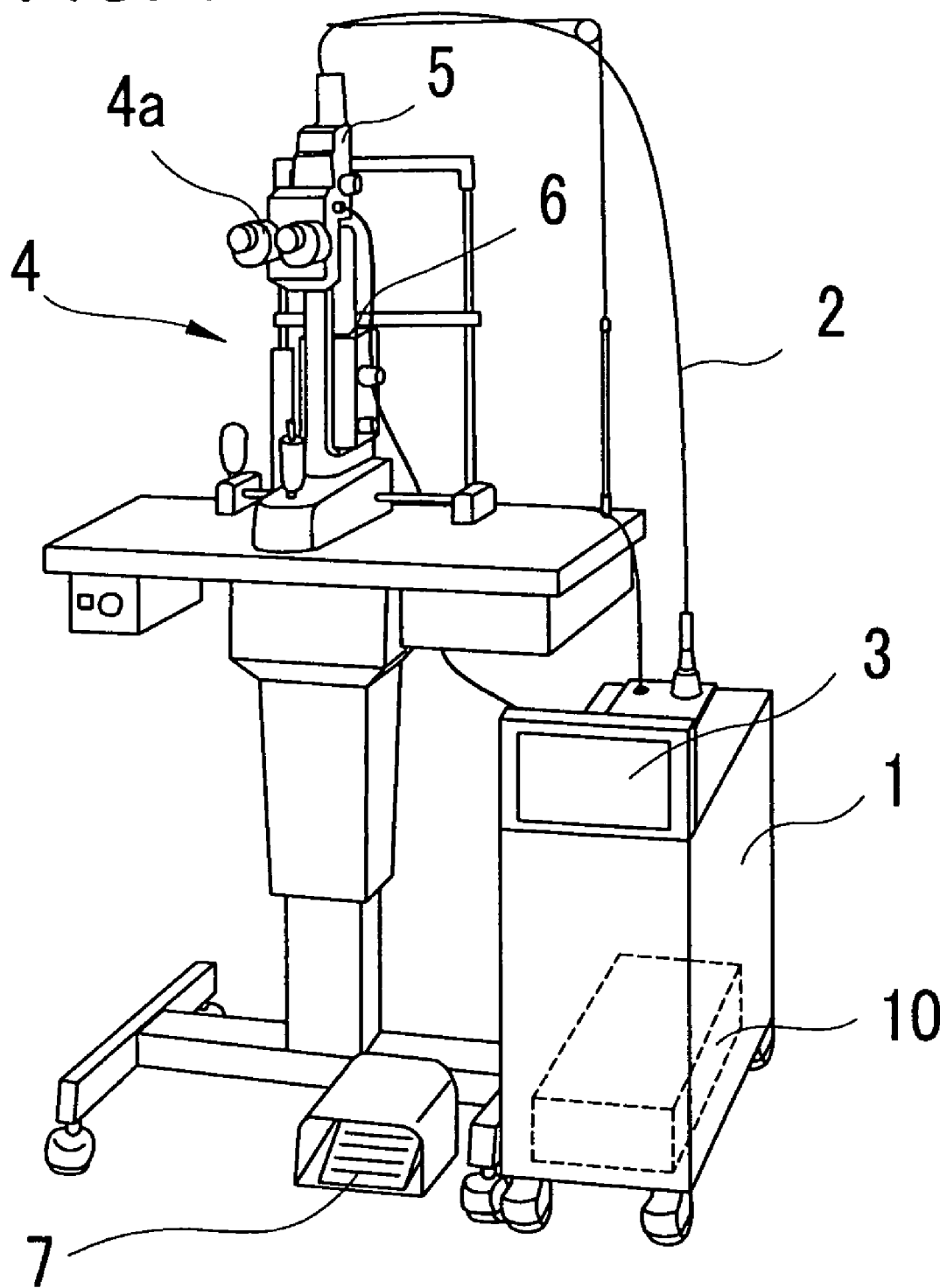
FIG. 1 is a schematic view of an external configuration of a laser treatment apparatus.

A detailed description of a preferred embodiment of the present invention will now be given referring to the accompanying drawings. FIG. 1 is a schematic view of an external configuration of a laser treatment apparatus. A main body 1 internally contains an optical system unit 10 (see FIG. 2) including a plurality of laser sources removably placed and an optical system for delivering a laser beam into an optical fiber 2. The optical system unit 10 is placed so as to be taken out from the main body 1 through a back door thereof. On top of the main body 1, a control panel 3 with a built-in color liquid crystal display of touch panel type is provided. The control panel 3 allows setting of a mounting state of each of a plurality of treatment laser sources as well as input and display of laser irradiation conditions such as laser power, irradiation time, etc. The control panel 3 therefore serves as both a display unit for displaying various information and an input unit for inputting various signals corresponding to the displayed information.

Furthermore, the laser treatment apparatus includes a slit lamp 4 for allowing a doctor (a user) to irradiate a laser beam to an affected part while observing a patient's eye, a laser irradiation part 5 attached to the slit lamp 4 and configured to irradiate the laser beam delivered through the optical fiber 2, and a footswitch 7 for sending a trigger signal to start laser irradiation. The slit lamp 4 is provided with an illumination part 6 for illuminating the patient's eye and a binocular microscope 4a through which the patient' eye is observed.

Figure 2:
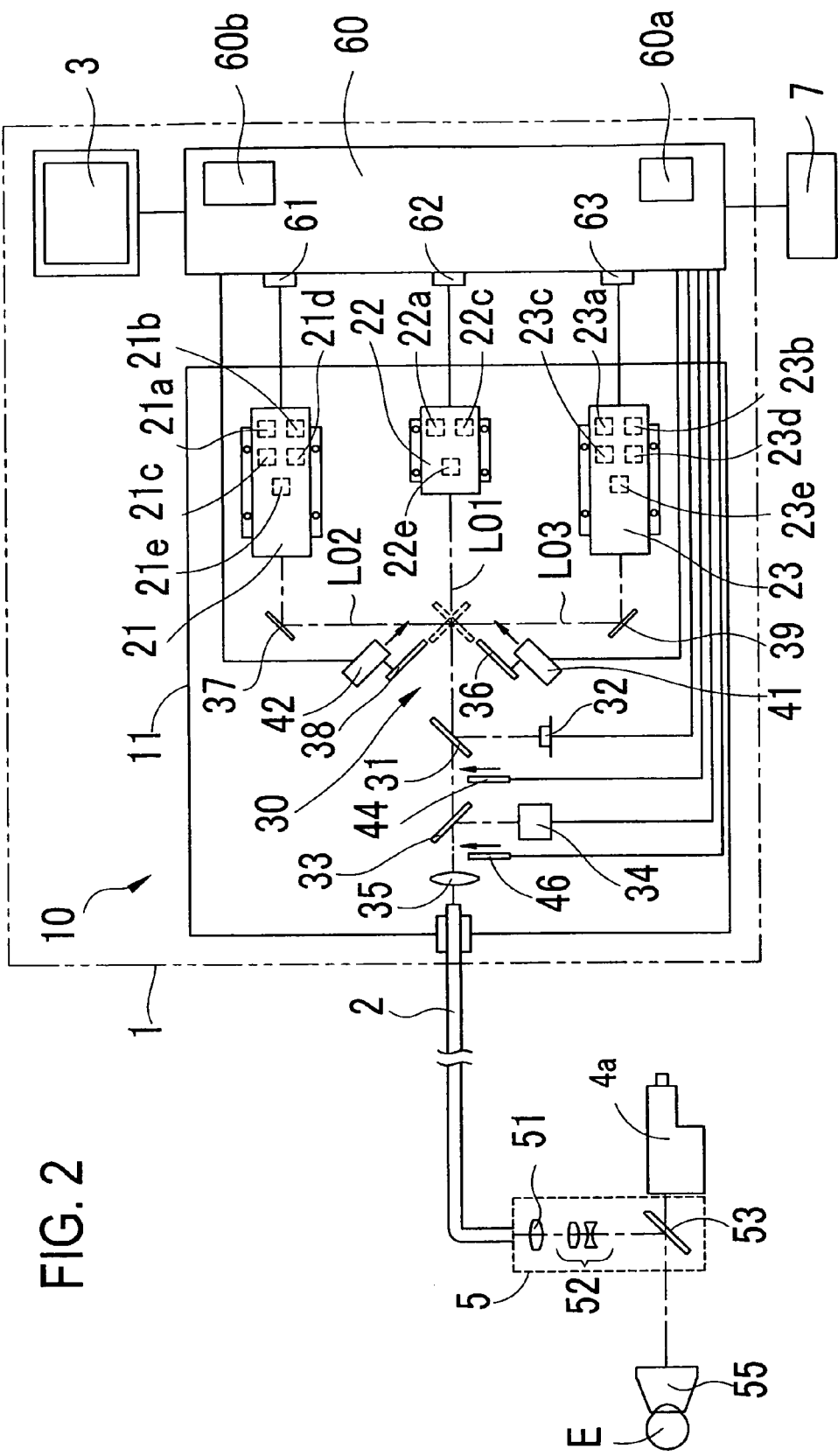
FIG. 2 is a schematic configuration view of an optical system and a control system.

FIG. 2 is a schematic configuration view of the optical system and a control system arranged in the optical system unit 10. On a base 11 of the optical system 10, three treatment laser sources 21, 22, and 23 are mounted. The laser sources 21, 22, and 23 can be respectively mounted in and dismounted from respective predetermined places on the base 11 with fixing members such as screws. For instance, the laser source 21 is a green laser source that emits a green laser beam having a wavelength of 532 nm. Inside the laser source 21, there are placed a solid-state laser medium such as an Nd:YAG crystal, an excitation light source such as a semiconductor laser, a wavelength converting element for converting light of a wavelength of 1064 nm emitted from the solid-state laser medium to light of a wavelength of 532 nm, and a pair of full reflection mirror and output mirror for resonating the light from the solid-state laser medium. The laser source 22 is a red laser source that emits a red laser beam having a wavelength of 647 nm and is constituted of for example a semiconductor laser source. The laser source 23 is a yellow laser source that emits a yellow laser beam having a wavelength of 561 nm. Inside the laser source 23, as with the laser source 21, there are placed a solid-state laser medium such as an Nd:YAG crystal, an excitation light source such as a semiconductor laser, a wavelength converting element for converting light of a wavelength of 1123 nm emitted from the solid-state laser medium to light of a wavelength of 561 nm, and a pair of full reflection mirror and output mirror for resonating the light from the solid-state laser medium.

The laser source 21 is provided with cooling devices 21a and 21b such as Peltier elements for cooling the excitation light source and the wavelength converting element respectively, and temperature sensors 21c and 21d for detecting temperatures of the excitation light source and the wavelength converting element respectively. The laser source 22 is provided with a cooling device 22a such a Peltier element for cooling the semiconductor laser, and a temperature sensor 22c for detecting a temperature of the semiconductor laser. The laser source 23 is also provided with cooling devices 23a and 23b for cooling the excitation light source and the wavelength converting element respectively and temperature sensors 23c and 23d for detecting temperatures of the excitation light source and the wavelength converting element respectively. A signal representing a detected temperature from the temperature sensor of each laser source is transmitted to a control unit 60 mentioned later. The control unit 60 monitors the temperature of each element in the laser sources 21, 22, and 23 and drives the cooling devices 21a, 21b, 23a, and others placed in corresponding laser sources to keep each temperature at a permissible temperature.

A treatment laser beam emitted from each of the laser sources 21, 22, and 23 is delivered to the patient's eye through a light delivery optical system 30 having the following configuration. An optical axis L01 along which the laser beam emitted from the laser source 22 travels is a common optical path for laser beams from the three laser sources 21, 22, and 23. On the optical axis L01, a beam splitter 31 which reflects part of a laser beam, a dichroic mirror 33, and a condensing lens 35 are disposed. The laser beam reflected by the beam splitter 31 is received by a power sensor 32 for output power monitoring. The dichroic mirror 33 has a property of reflecting a beam (a dominant wavelength of 670 nm) emitted from a visible-light semiconductor laser source 34 for aiming and transmitting each laser beam (wavelengths of 532 nm, 647 nm, and 561 nm) from the three treatment laser sources 21, 22, and 23. The beam emitted from the visible-light semiconductor laser source 34 is coaxially combined, by the dichroic mirror 33, with the treatment laser beam traveling along the optical axis L01.

Mirrors 36 and 38 are arranged to be inserted on and retreated from the optical axis L01 between the laser source 22 and the beam splitter 31. By the mirror 36, the green laser beam emitted from the laser source 21 and reflected by a mirror 37 to travel along an optical axis L02 is deflected to the optical axis L01. The mirror 36 is moved by a drive unit 41 to be selectively inserted on the optical axis L01. By the mirror 38, the yellow laser beam emitted from the laser source 23 and reflected by a mirror 39 to travel along an optical axis L03 is deflected to the optical axis L01. The mirror 38 is moved by a drive unit 42 to be selectively inserted on the optical axis L01. Each of the drive units 41 and 42 can be configured by a well known mechanism having a motor and a sliding mechanism, etc. Furthermore, the drive units 41 and 42 may be configured by a common drive unit.

A coagulation shutter 44 for blocking a treatment laser beam for coagulation is placed to be inserted on and retreated from the optical path located between the beam splitter 31 and the dichroic mirror 33. A safety shutter 46 is placed to be inserted on and retreated from the optical path located between the dichroic mirror 33 and the condensing lens 35. In case of an abnormal circumstance, the safety shutter 46 is inserted on the optical axis L01.

Each laser beam traveling along the optical axis L01 is condensed by the condensing lens 35 to enter the optical fiber 2. Each laser beam delivered through the optical fiber 2 is directed to the patient's eye E through a collimating lens 51, zoom lenses 52, and a mirror 53, and then delivered to the eye E through a contact lens 55. The doctor (the user) observes the eye E through an observation optical system of the binocular microscope 4a in the slit lamp 4.

The laser sources 21, 22, and 23 are connected to the control unit 60 through connectors 61, 62, and 63, respectively. The control unit 60 includes a power source unit 60b for supplying drive electric current to each laser source 21, 22, and 23. When the connectors 61, 62, and 63 are connected to the control unit 60, the control unit 60 supplies electric current to each of the laser sources 21, 22, and 23 to control respective driving conditions. Based on output signals representing the temperatures detected by the temperature sensors 21c, 22c, and 23c placed in the laser sources through the connectors 61, 62, and 63, the control unit 60 further controls driving of the cooling devices 21a, 22a, and 23a and others to bring each element in each laser source to a predetermined temperature. The temperature detection signals from the temperature sensors 21c, 22c, and 23c are utilized as a predetermined operation check signal of each laser source.

The above configured apparatus is explained below with a focus on operations for selectively mounting the three laser sources 21, 22, and 23 in the optical system 10 of the main body 1. At a manufacturing stage of the laser treatment apparatus, three laser sources 21, 22, and 23 are selectively mounted in the main body in accordance with an order from an ophthalmic clinic or hospital (a doctor) or a production planning. At this time, the control unit 60 is operated on a manufacturer's side to recognize which laser source(s) is mounted in the main body 1 (the base 11).

Figure 3:
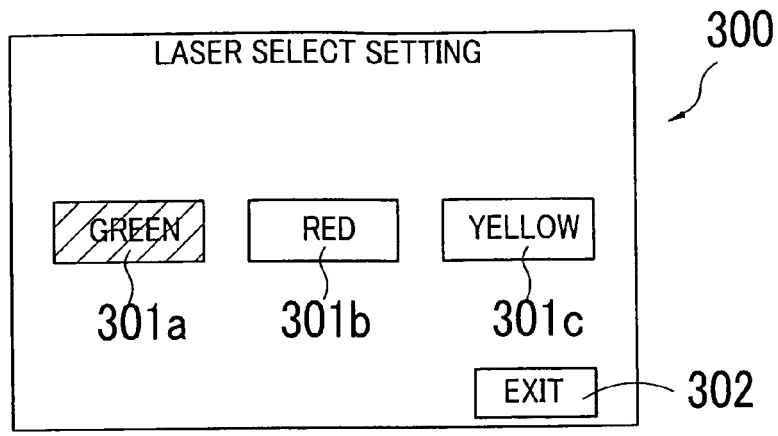
FIG. 3 is an example of a setting screen displayed on a control panel

FIG. 3 shows an example of a setting screen to be displayed on the control panel 3 to set which one(s) of the laser sources 21, 22, and 23 are mounted in the main body 1. This setting screen 300 is displayed when a custom mode is selected from an operation mode selection menu on an initial screen appearing on the control panel 3 upon activation of the apparatus.

On the screen 300 in FIG. 3, there appear a "GREEN" switch 301a, a "RED" switch 301b, and a "YELLOW" switch 301c. The switches 301a, 301b, and 301c correspond to the green laser source 21, the red laser source 22, and the yellow laser source 23 respectively. Each switch, whenever pressed, is switched between ON or OFF states. To set the laser sources 21, 22, and 23 mounted in the main body 1, a manufacturer's operator turns each switch 301a, 301b, and 301c into the ON state. When the switches 301a, 301b, and 301c are turned ON, respective display colors are reversed with respect to a background color of the screen 300, informing the operator of a selection status of each laser source. The manufacturer's operator who knows which laser source(s) has been mounted can select the switch(es) accurately. A setting signal representing the mounting state(s) of the selected one(s) of the laser sources 21, 22, and 23 by the switches 301a, 301b, and 301c is input to the control unit 60. The setting information is stored in a memory 60a of the control unit 60. After completion of selection of the laser source(s), when the operator presses an EXIT switch 302, the screen 300 is switched to the initial screen.

The following explanation is given to operations of the laser treatment apparatus in use. When the power of the main body 1 is turned on (at the time of activation of the apparatus), the control unit 60 performs an initial operation check to check whether an abnormality is present or not in each laser source based on a predetermined operation check signal from each laser source. At this time, based on the mounting state of each laser source 21, 22, and 23 set on the setting screen 300 in FIG. 3 and stored in the memory 60a, the predetermined operation check is conducted about the laser source(s) mounted in the main body 1. For instance, in the case where only the laser source 21 is mounted, the control unit 60 supplies weak electric current to the laser source 21 for the operation check. The control unit 60 then drives the cooling devices 21a and 21b based on input of the temperature detection signals from the temperature sensors 21c and 21d to bring the temperature of the element in the laser source 21 to a predetermined temperature. At this time, the control unit 60 checks whether or not the detected temperatures by the temperature sensors 21c and 21d are changing toward the predetermined temperature.

Herein, the temperature detection signals from the temperature sensors 21c and 21d are utilized as the operation check signal of the laser source 21. In case the temperatures detected by the temperature sensors 21c and 21d are abnormal (e.g., in a case where each temperature does not change toward the predetermined temperature), the control unit 60 judges that driving of the laser source 21 or temperature control by the cooling devices 21a and 21b is abnormal, and displays an error message of warning to that effect on the display screen of the control panel 3. The safety shutter 46 is closed to block the laser beam from going out of the main body. The operation of the apparatus is thus stopped.

On the other hand, based on the mounting information of each laser source 21, 22, and 23, the control unit 60 stops the check control to check whether an abnormality is present or not in relation to the aforementioned initial operation check on the laser sources 22 and 23 not mounted in the main body 1. Herein, if the control unit 60 has not recognized the mounting information about each laser source 21, 22, and 23, the control unit 60 will conduct the aforementioned operation check even on the laser sources 22 and 23 not actually mounted. In this case where the laser sources 22 and 23 are unmounted, an unnecessary error warning is generated, which causes an unfavorable result that the operation of the apparatus is stopped. On the other hand, in the present embodiment in which the control unit 60 has recognized in advance which laser source is mounted in the main body 1, such unnecessary trouble can be avoided and the user (the doctor) is allowed to use the laser apparatus appropriately.

The initial operation check on each laser source 21, 22, and 23 at the time of activation of the apparatus may be conducted not only by use of the temperature sensors 21c, 21d, 22c, 23c and 23d but also by any other means. For instance, the laser sources 21, 22, and 23 are provided with current detectors 21e, 22e, and 23e, respectively, for detecting whether or not electric current is supplied from the power source unit 60b through respective connectors 61, 62, and 63. In the case where only the laser source 21 is mounted as with the above case, the control unit 60 supplies weak electric current for operation check to the laser source 21. At this time, if the current detector 21e detects that the electric current is supplied, a check signal thereof is transmitted to the control unit 60. In the case where no detection signal is transmitted from the current detector 21e, the control unit 60 judges that a power supply line or the like in the laser source 21 is abnormal, and displays an error message of warning to that effect on the display screen of the control panel 3. The control unit 60 further closes the safety shutter 46 to block the laser beam from going out of the main body 1 and stops the operation of the apparatus.

As another means for the initial operation check, the power sensor 32 for output power monitoring may be utilized. At the time of activation of the apparatus, the control unit 60 maintains the coagulation shutter 44 and the safety shutter 46 in a closed state and emits a laser beam by sequentially driving only the laser source(s) mounted in the main body 1 based on the mounting information of each laser source. In the case where no laser output for test emission is detected by the power sensor 32, the concerned laser source is judged to be abnormal, and a warning is displayed on the control panel 3. As to the laser source(s) unmounted in the main body 1, the control unit 60 stops (disables) the initial operation check to check whether an abnormality is present or not. Accordingly, it is possible to avoid an unnecessary trouble that emits an error warning about the laser source(s) unmounted in the main body 1.

Figure 4A:
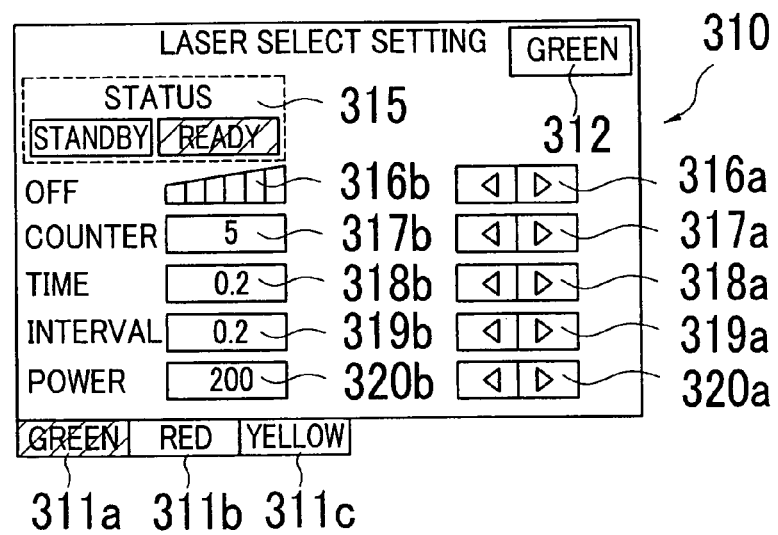
FIG. 4A is an example of an input screen for laser irradiation conditions when green, red, and yellow laser sources are mounted.

Operations for laser treatment are explained below. FIG. 4A is an example of an input screen for laser irradiation conditions to be displayed on the control panel 3 during treatment. The example in FIG. 4A shows the case where the setting that all the three laser sources 21, 22, and 23 are mounted is made on the screen 300 in FIG. 3. In this case, under an input screen 310, a green laser selection switch 311a, a red laser selection switch 311b, and a yellow laser selection switch 311c appear to select a wavelength of a laser beam to be used for treatment. Which color (wavelength) of the laser beams is selected is informed to the operator by changing of the display color of the selected one of the switches 311a to 311c. For instance, when the green laser beam is selected by the switch 301a, the color of the switch 301a is reversed. In an indication box 312 appearing at an upper part of the input screen 310, the selected laser beam color (wavelength) by one of the switches 311a to 311c is indicated.

Herein, the display of the selection switches 311a, 311b, and 311c as laser beam selection means (the display on the control panel 3) is controlled by the control unit 60 based on the setting information representing the mounting states of the laser sources 21, 22, and 23 stored in the memory 60a. In FIG. 4A, showing that all the laser sources 21, 22, and 23 are mounted, the corresponding selection switches 311a, 311b, and 311c are displayed.

Figure 4B:
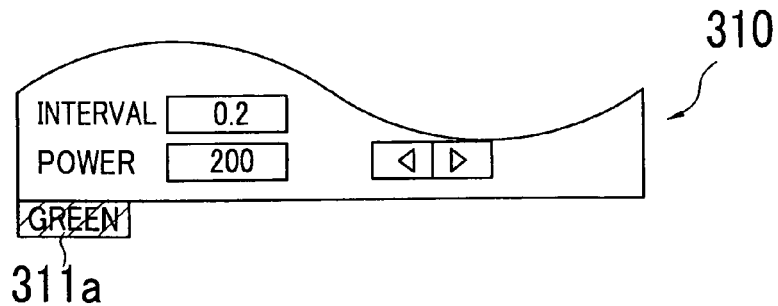
FIG. 4B is an example of an input screen for laser irradiation conditions when only the green laser source is mounted.
Figure 4C:
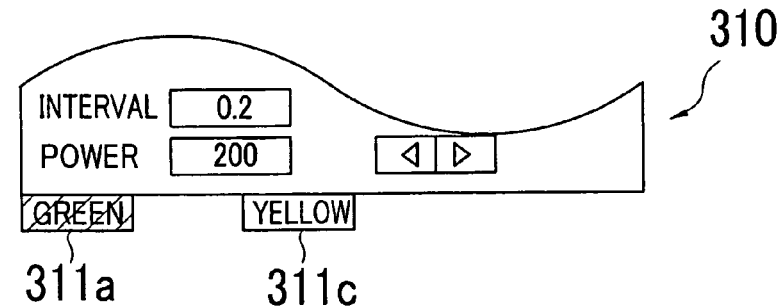
FIG. 4C is an example of an input screen for laser irradiation conditions when the green and yellow laser sources are installed.

On the other hand, FIG. 4B shows the case where only the green laser source 21 is mounted. In this case, the display on the control panel 3 is controlled to display only the selection switch 311*a* corresponding to the green laser source 21 and not to display the switches 311*b* and 311*c*. FIG. 4C shows the case where the green laser source 21 and the yellow laser source 23 are mounted. In this case, the display on the control panel 3 is controlled to display the switches 311*a* and 311*c* corresponding to the green laser source 21 and the yellow laser source 23 respectively and not to display the switch 311*b* corresponding to the red laser source 22. In this way, based on the setting information about the mounting states of the laser sources 21, 22, and 23, selection of the laser source(s) unmounted in the main body is disabled. This makes it possible to prevent the user (the doctor) from erroneously selecting the wavelength(s) of the laser source(s) unmounted in the main body. Furthermore, it is possible to avoid unnecessary confusion for the user (the doctor) who has not know the mounting state(s) of the laser source(s).

In FIG. 4A, the input screen 310 for laser irradiation conditions includes a STATUS switch 315 for inputting a status of enabling/disabling laser irradiation, a switch 316*a* for inputting brightness level of the aiming beam, an indication box 316*b* for indicating the level of the aiming beam, a switch 317*a* for inputting the number of irradiations of the laser beam, an indication box 317*b* for indicating the number of the irradiations of the laser beam, a switch 318*a* for inputting an irradiation time of the laser beam to be irradiated by one trigger signal, an indication box 318*b* thereof, a switch 319*a* for inputting a halt time of the laser beam during continuous irradiation of the laser beam, an indication box 319*b* for displaying the halt time, a switch 320*a* for inputting output power of the laser beam, and an indication box 320*b* thereof.

When the green laser beam is selected on the input screen 310 as mentioned above, for example, the control unit 60 drives the drive unit 41 to move the mirror 36 onto the optical axis L01. The aiming beam emitted from the visible light semiconductor laser 34 is delivered to the optical system of the laser irradiation part 5 through the optical fiber 2 and then irradiated to the fundus of the patient's eye E. The operator observes the fundus of the eye E through the binocular microscope 4*a* and makes alignment of an irradiation spot of the aiming beam to a part to be treated. A spot size of the laser beam to be irradiated to the patient's eye E can be adjusted to a desired size by moving the zoom lenses 52 placed in the laser irradiation part 5. After completion of the alignment of the aiming beam to the treatment part, the control unit 60, upon receipt of the trigger signal from the footswitch 7 pressed by the user (the doctor), moves the coagulation shutter 44 out of the optical axis L01 to enable deliver of the treatment laser beam. The green laser beam emitted from the laser source 21 is reflected by the mirror 36, passes through the beam splitter 31 and the dichroic mirror 33, and enters the optical fiber 2 by the condensing lens 35. The laser beam emerging from the optical fiber 2 passes through the optical system in the laser irradiation part 5 and then is irradiated to the treatment part under alignment by the aiming beam.

In the case where the yellow laser beam is selected, the control unit 60 moves the mirror 36 out of the optical axis L01 and then drives the drive unit 42 to place the mirror 38 on the optical axis L01. This allows the yellow laser beam emitted from the laser source 23 to enter the optical fiber 2 and be delivered to the treatment part. In the case where the red laser beam is selected, the control unit 60 moves both the mirrors 36 and 38 out of the optical axis L01. This allows the red laser beam emitted from the laser source 22 to enter the optical fiber 2 and be delivered to the treatment part.

As explained above, one(s) of the laser sources 21, 22, and 23, having a wavelength(s) desired by the ophthalmic clinic or hospital (the doctor) can be selected and mounted in the main body 1, so that unnecessary troubles can be prevented in use. When the doctor desires only the green laser, for example, a laser treatment apparatus in which only the laser source 21 is mounted in the main body 1 is offered. If the doctor needs the yellow laser beam afterward, the laser source 23 that emits the yellow laser can be additionally mounted in the main body 1 in which the laser source 21 that emits the green laser has been initially mounted. It is therefore economic advantageous for the doctor who bought this apparatus.

In the case where the laser source(s) is added, the manufacturer's side uses the setting screen 300 in FIG. 3 to update the mounting information of the laser sources stored in the memory 60*a*, whereby the control unit 60 recognizes again which laser sources are mounted in the main body 1. Even when the laser source(s) is added, accordingly, the aforementioned initial operation check is adequately conducted, thereby avoiding unnecessary troubles in use. Furthermore, only the laser source(s) mounted in the main body 1 is permitted to be selected, which enables the doctor to appropriately perform treatment using the laser beam having a desired wavelength without confusion.

The following explanation is given to a modified example of a configuration for inputting a setting signal to set which one(s) of the laser sources mountable in the main body 1 are mounted. In the above example, the setting screen 300 of FIG. 3 is displayed on the control panel 3 to allow the operator to input the setting signal representing the mounting information of the laser source(s). The following is an example to automatically detect which one(s) of the laser sources is mounted.

Figure 5A:
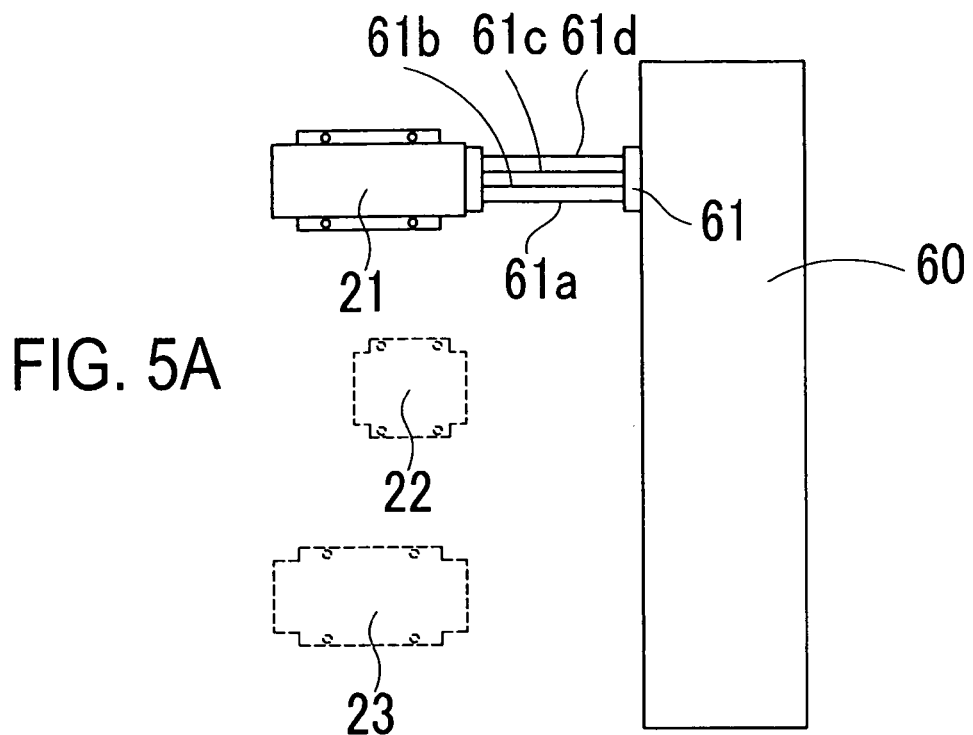
FIG. 5A is a view to explain a method of recognizing a laser source by use of wires of a connector that connects each laser source and a control unit.

FIG. 5A is an explanatory view to show a detection method utilizing wires of the connectors 61, 62, and 63 for connecting the laser sources 21, 22, and 23 to the control unit 60. In FIG. 5A, main wires of the connector 61 for connecting the laser source 21 to the control unit 60 include an electric wire 61*a* for supplying electric current from the power source unit, a wire 61*b* for temperature control to be connected to the cooling device 21*a* (21*b*), and a wire 61*c* for temperature monitoring to be connected to the temperature sensor 21*c* (21*d*). In addition to those wires, a wire 61*d* for laser recognition is provided to allow the control unit 60 to detect the mounting state of the laser source 21. When the connector 61 is connected to the control unit 60, the laser recognition wire 61*d* is connected to the control unit 60. At the time of activation of the main body 1, when the laser recognition wire 61*d* has been connected, a "Low" level signal is input to the control unit 60. When the laser recognition wire 61*d* has not been connected, a "High" level signal is input to the control unit 60. Accordingly, the control unit 60 detects the presence or absence of the laser source 21. Similarly, the connector 62 of the laser source 22 and the connector 63 of the laser source 23 are also each provided with a wire for laser recognition. The control unit 60 thus detects the presence or absence of the laser sources 21 and 23 based on whether or not respective laser recognition wires are connected to the control unit 60. In other words, the control unit 60 also serves as a detection unit for detecting the presence or absence of the laser source(s) by detecting electrical connection to the laser source(s). The control unit 60 automatically inputs a setting signal representing which laser source(s) is mounted based on the above detection result(s) and stores the mounting information of the laser source(s) in the memory 61*a*.

Figure 5B:
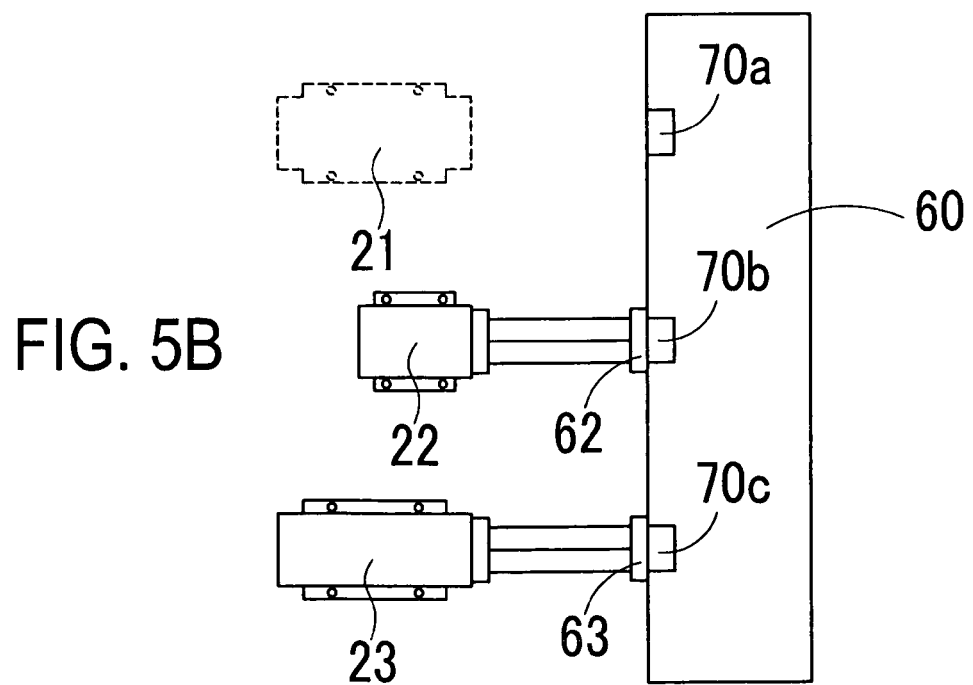
FIG. 5B is a view to explain a method of recognizing a laser source by use of an electric wire.

Alternatively, the control unit 60 can set the mounting information of the laser source(s) by use of the electric wire 61a without providing the laser recognition wire 61d. FIG. 5B is a method of using the electric wire 61 to let the control unit 60 recognize the presence or absence of connection to the connectors 61, 62, and 63 of the laser sources 21 to 23. In this case, current detectors 70a, 70b, and 70c for detecting electric current are provided between the laser sources 21 to 23 and the control unit 60 respectively. Upon activation of the apparatus, the control unit 60 operates to supply a fixed amount of electric current to each laser source mounted in the main body 1. In the case where each current detector 70a, 70b, and 70c is supplied with the electric current, each detection signal is transmitted to the control unit 60. In the opposite case where no electric current is supplied, any detection signal is not transmitted. The control unit 60 thus sets the mounting state of each laser source 21, 22, and 23.

Furthermore, various sensors for physically detecting the presence or absence of each laser source may be provided, so that the control unit 60 can recognize the mounting state of each laser source. In FIG. 6, the base 11 has predetermined spaces 15, 16, and 17 in which the laser sources 21, 22, and 23 will be respectively mounted. In the spaces 15-17, microswitches 72a, 72b, and 72c are placed respectively. When each laser source 21 to 23 is put in each corresponding space 15 to 17, a switch signal of each microswitch 72a to 72c is turned ON whereby the presence of each laser source 21 to 23 is detected. The detection signal(s) thereof is transmitted to the control unit 60. The control unit 60 recognizes (sets) the mounting state of each laser source based on the detection signal from each microswitch 72a to 72c.

Instead of the microswitches, a reflection-type sensor such as a photointerrupter for detection using light may be used. The reflection-type sensor is preferably provided in a place favorable to sufficiently detect the mounting state, e.g., in the vicinity of a side surface of each laser source.

The invention claimed is:

1. A laser treatment apparatus for irradiating a laser beam to a patient's eye, comprising:
    an optical fiber;
    a main body having a base;
    a plurality of laser sources which emit treatment laser beams having different wavelengths, each laser source being detachable mounted on the base of the main body and connected to a power source through a connector;
    a light delivery optical system that delivers the treatment laser beams to the optical fiber, the light delivery optical system having a mirror for making the treatment laser beams from the laser sources coaxial with each other to deliver each treatment laser beam to the optical fiber;
    an input unit for inputting mounting information of each laser source, the mounting information including information indicating the laser source mounted on the base, of the mountable laser sources, and the input unit being able to change the mounting information when one of the plurality of laser sources is subsequently mounted to or demounted from the main body;
    an irradiation optical system configured to irradiate the treatment laser beam emerged from the optical fiber to the patient's eye;
    an irradiation condition setting unit including a display and being arranged to display a screen for setting an irradiation condition of the treatment laser beam on the display;
    a selection unit for selecting one of the laser sources for irradiating the treatment laser beam to the patient's eye, the selection unit being arranged to display the selectable laser beam based on the mounting information on the setting screen; and
    a control unit which checks a predetermined operation of each laser source by a sensor at the time of activation to determine whether an abnormality is present or not in each laser source, and displays an indication that the abnormality is present on a display, the control unit driving the selected laser source based on a trigger signal even when a part of the plurality of laser sources are not mounted on the base, and irradiating the laser beam according to the irradiation condition.

2. The laser treatment apparatus according to claim 1, wherein the input unit includes a switch for inputting a signal representing the mounting information of each laser source.

3. The laser treatment apparatus according to claim 1, wherein the input unit includes a detection unit for detecting the presence or absence of the laser source or laser sources mounted on the base, and automatically inputs a signal representing the mounting information based on a detection result of the detection unit.

4. The laser treatment apparatus according to claim 3, wherein the detection unit includes a sensor for detecting electrical connection to each laser source, or a sensor for physically detecting whether or not each laser source is placed in a predetermined position on the base.

5. The laser treatment apparatus according to claim 1, wherein
    the control unit checks whether or not an abnormality is present in each laser source based on a predetermined operation check signal to be output from each laser source when electric power is supplied to each laser source mounted on the base at the time of activation of the apparatus or a detection signal of the output sensor when the treatment laser beam is emitted for test by driving each laser source, and the control unit causes the display to display an indication that the abnormality is present when the abnormality is detected, and changes the laser source to be checked as to whether or not an abnormality is present based on the mounting information when the mounting information set by the mounting information setting unit is changed.

6. A laser treatment apparatus for irradiating a laser beam to a patient's eye, comprising:
    an optical fiber;
    a main body containing a base on which a plurality of laser sources are detachably mounted and a light delivery optical system for delivering a treatment laser beam to the optical fiber;
    an irradiation optical system configured to irradiate the treatment laser beam emerged from the optical fiber to the patient's eye;
    an irradiation condition setting unit including a display and being arranged to display a screen for setting an irradiation condition of the treatment laser beam on the display;
    a mounting information setting unit for setting mounting information of the laser source, the mounting information including information indicating the laser source mounted on the base, of the mountable laser sources, and the mounting information setting unit being able to change the mounting information when one of the plurality of laser sources is subsequently mounted to or demounted from the main body;
    a selection unit for selecting one of the laser sources for irradiating the treatment laser beam to the patient's eye, the selection unit being arranged to display the selectable laser beam based on the mounting information on the setting screen; and a control unit for driving the selected laser source based on a trigger signal even when a part of the plurality of laser sources are not mounted on the base, and irradiating the laser beam according to the irradiation condition.

7. The laser treatment apparatus according to claim 6, wherein the mounting information setting unit includes a switch for inputting a signal representing the mounting information of each laser source.

8. The laser treatment apparatus according to claim 6, wherein the mounting information setting unit includes a detection unit for detecting the presence or absence of the laser source or laser sources mounted on the base, and automatically inputs a signal representing the mounting information based on a detection result of the detection unit.

9. The laser treatment apparatus according to claim 8, wherein the detection unit includes a sensor for detecting electrical connection to each laser source, or a sensor for physically detecting whether or not each laser source is placed in a predetermined position on the base.

10. The laser treatment apparatus according to claim 6, wherein the control unit checks whether or not an abnormality is present in each laser source based on a predetermined operation check signal to be output from each laser source when electric power is supplied to each laser source mounted on the base at the time of activation of the apparatus or a detection signal of the output sensor when the treatment laser beam is emitted for test by driving each laser source, and the control unit causes the display to display an indication that the abnormality is present when the abnormality is detected, and changes the laser source to be checked as to whether or not an abnormality is present based on the mounting information when the mounting information set by the mounting information setting unit is changed.

* * * * *